(12) United States Patent
Kane

(10) Patent No.: US 12,151,063 B2
(45) Date of Patent: Nov. 26, 2024

(54) UTILIZING LOOP GAIN FOR POSITIVE AIRWAY PRESSURE VENTILATION

(71) Applicant: KONINKLIJKE PHILIPS N.V., Eindhoven (NL)

(72) Inventor: Michael Thomas Kane, Harrison City, PA (US)

(73) Assignee: KONINKLUKE PHILIPS N.V., Eindhoven (NL)

( * ) Notice: Subject to any disclaimer, the term of this patent is extended or adjusted under 35 U.S.C. 154(b) by 962 days.

(21) Appl. No.: 17/138,971

(22) Filed: Dec. 31, 2020

(65) Prior Publication Data

US 2021/0196914 A1 Jul. 1, 2021

Related U.S. Application Data

(60) Provisional application No. 62/955,492, filed on Dec. 31, 2019.

(51) Int. Cl.
*A61M 16/00* (2006.01)

(52) U.S. Cl.
CPC ...... *A61M 16/024* (2017.08); *A61M 16/0057* (2013.01); *A61M 2016/0027* (2013.01); *A61M 2016/003* (2013.01); *A61M 2230/40* (2013.01)

(58) Field of Classification Search
CPC ............ A61M 16/024; A61M 16/0057; A61M 2016/0027; A61M 2016/003;
(Continued)

(56) References Cited

U.S. PATENT DOCUMENTS 9,044,560 B2   6/2015   Shelly
9,463,293 B2 * 10/2016  Shelly ............... A61M 16/0009
(Continued)

FOREIGN PATENT DOCUMENTS

WO     0045882 A1    8/2000
WO  2016065411 A1    5/2016
WO  2018204985 A1   11/2018

OTHER PUBLICATIONS

Andrew Wellmane et al. "A Method for Measuring and Modeling He Physiological Traits Causing Obstructive Sleep Apnea", J Appl Physiol 110: 1627-1637. 2011.
(Continued)

*Primary Examiner* — Michael R Reid
*Assistant Examiner* — Tina Zhang

(57) ABSTRACT

A system for delivering a flow of gas to an airway of a patient respiratory system includes a gas flow generator, a sensor, and a loop gain controller. The loop gain controller selectively controls the flow of gas to the airway according to a positive airway pressure (PAP) therapy mode. The loop gain controller comprises (a) a stability metric module, (b) a condition monitoring module that monitors ventilation characteristics of the flow of gas in the patient respiratory system and provides an output indicative of monitored
(Continued)

ventilation characteristics, (c) a loop gain decision module that determines a future ventilation characteristic target and plant gain target, (d) a therapy prescription decision module that determines a therapy command pressure or delivery characteristic, and (e) a pressure delivery module that controls the gas flow generator to deliver the flow of gas at the determined therapy command pressure or delivery characteristic for a future breath.

19 Claims, 5 Drawing Sheets

(58) Field of Classification Search
CPC .......... A61M 2230/40; A61M 16/0434; A61M 16/06; A61M 16/0672; A61M 16/1075; A61M 16/201; A61M 2016/0039; A61M 2016/0042; A61M 2202/0208; A61M 2205/18; A61M 2205/3334; A61M 2205/3368; A61M 2205/3584; A61M 2205/505; A61M 2205/52; A61M 2205/581; A61M 2205/582; A61M 2205/583; A61M 2210/1039; A61M 2230/205; A61M 2230/42; A61M 2230/46; A61M 16/0069; A61M 16/026; A61B 5/4806; A61B 5/4818; A61B 5/0205; A61B 5/113
See application file for complete search history.

(56) References Cited

U.S. PATENT DOCUMENTS

| 2003/0121519 | A1* | 7/2003 | Estes | A61M 16/0051 |
| | | | | 128/204.23 |
| 2007/0221224 | A1* | 9/2007 | Pittman | A61M 16/0069 |
| | | | | 128/203.14 |
| 2009/0050154 | A1* | 2/2009 | Strothmann | A61M 16/161 |
| | | | | 128/204.23 |
| 2013/0046151 | A1* | 2/2013 | Bsoul | A61B 5/4815 |
| | | | | 600/509 |

OTHER PUBLICATIONS

Scott A. Sands et al. "Loop Gain as a Means to Predict a Positive Airway Pressure Suppression of Cheyne-Stokes Resppiration in Patients With Heart Failure", pp. 1-26. On Line Data Supplement.
Scott A. Sands et al. "Loop Gain as a Means to Predict a Positive Airway Pressure Suppression of Cheyne-Stokes Resppiration in Patients With Heart Failure", Am J Respir Crit Care Med, vol. 184, pp. 1067-1075, 2011.
Nemati Shamim et al: "Model-Based Characterization of Ventilatory Stability Using Spontaneous Breathing", Journal of Applied Physiology, vol. 111, No. 1, Jul. 1, 2011.
Deacon-Diaz Naomi et al: "Inherent vs. Induced Loop Gain Abnormailities in Obstructive Sleep Apnea", Frontiers in Neurology, vol. 9, Nov. 2, 2018.

* cited by examiner

UTILIZING LOOP GAIN FOR POSITIVE AIRWAY PRESSURE VENTILATION

TECHNICAL FIELD

The present embodiments relate generally to a system and method for positive airway pressure therapy and more particularly, to a system and method for positive airway pressure therapy utilizing loop gain for ventilation stability.

BACKGROUND

Congestive heart failure (CHF) patients commonly suffer from respiratory disorders, such as obstructive sleep apnea (OSA) or central apneas. Another such respiratory disorder that CHF patients often experience during sleep is known as Cheyne-Stokes respiration. FIG. 1 illustrates a typical Cheyne-Stokes respiration (CSR) pattern 30, which is characterized by rhythmic waxing periods 32 and waning periods 34 of respiration, with regularly recurring periods of high respiratory drive (hyperpnea) 36 and low respiratory drive (hypopnea or apnea) 38. A typical Cheyne-Stokes cycle, generally indicated at 40, lasts about one minute and is characterized by a crescendo (arrow A), in which the peak respiratory flow of the patient increases over several breath cycles, and decrescendo (arrow B), in which the peak respiratory flow of the patient decreases over several breath cycles. The typical Cheyne-Stokes cycle ends with a central apnea or hypopnea following the decrescendo phase. Apneas, hyperpneas, and the abnormal change in the depth and rate of breathing often cause arousals and, thus, degrades sleep quality. This disruption in sleep, as well as the periodic desaturation of arterial oxygen, caused by the CSR cycle stresses the cardio-vascular system and specifically the heart.

The earliest treatment for CSR involved stimulating the respiratory drive by administering Theophyline, caffeine, or 1-3% inspired carbon dioxide to the patient. Although sometimes effective in reducing CSR, the downside of these treatments, which increase the respiratory rate, is that the increase in respiratory rate proportionally increases cardiac and respiratory workload.

Recent work in the treatment of sleep apnea and related breathing disorders has included bi-level positive airway therapy. In bi-level therapy, pressure is applied alternately at relatively higher and lower prescription pressure levels within the airway of the patient so that the therapeutic air pressure is alternately administered at a larger and smaller magnitude. The higher and lower magnitude positive prescription pressure levels are known as inspiratory positive airway pressure (IPAP) and expiratory positive airway pressure (EPAP), respectively. The inspiratory and expiratory pressure are synchronized with the patient's inspiratory cycle and expiratory cycle, respectively.

Some preliminary investigations reveal that cardiac output improves when patients are supported using bi-level pressure therapy. It has also been recognized that CSR can be treated by augmenting respiratory effort with positive pressure support when the CSR pattern is in hypopnea region 38. To accomplish this, it is known to use a ventilator or pressure support system to deliver machine triggered breaths during the hypopnea interval when the patient's own respiratory drive is reduced or not present. Alternatively, another method of treating CSR is where $CO_2$ is selectively rebreathed during the hyperneic phase of the CSR cycle. However, this method requires additional equipment to be used with the typical ventilator system.

In addition to the above, one of the first published works involving the modeling of the human respiratory system including the use of a digital computer is "A mathematical model of the human respiratory control system": Milhorn, Benton, Ross, Guyton: 1965. In that study, Milhorn et al. create a system schematic of the respiratory system and derive a series of time domain equations describing the interactions of each of the subsystems. In addition, a 1982 publication by Khoo et al. discloses the creation of a mathematical model for Cheyne-Stokes respiration or breathing (CSR). The publication by Khoo et al. begins to create an elaborate control system-based approach to this problem of modeling of the human respiratory system.

In 2010, Wellman et al. describe an experiment where several participants had data collected and a model was generated and fit to describe loop gain response at several plant conditions. In 2014, Terrill et al. continued the loop gain quantification work on data collected without intervention.

While each of the above-mentioned efforts (i.e., as discussed in the Background) have been useful in an attempt to understand, quantify and test one's own understanding of the human respiratory system, there exists a need for an improved method and apparatus of positive airway pressure therapy for overcoming the problems in the art.

SUMMARY

In accordance with one aspect, a system for delivering a flow of gas to an airway of a patient respiratory system is disclosed which includes a gas flow generator, at least one sensor, and a loop gain controller. The gas flow generator generates the flow of gas and communicates the flow of gas to a patient circuit for delivering the flow of gas to the airway of the patient respiratory system. The at least one sensor generates output signals related to at least one characteristic associated with the flow of gas. The loop gain controller selectively controls the flow of gas to the airway of the patient respiratory system according to a positive airway pressure (PAP) therapy mode, in response to the generated output signals. Flow into the airway of the patient respiratory system is positive flow and flow out of the airway of the patient respiratory system is negative flow, from the gas flow generator via the patient circuit. In addition, the PAP therapy mode is configured to treat a respiratory system loop gain deficiency corresponding to a ventilation instability by utilizing loop gain for ventilation stability.

The loop gain controller comprises (a) a stability metric module, (b) a condition monitoring module, (c) a loop gain decision module, (d) a therapy prescription decision module, and (e) a pressure delivery module. The stability metric module is configured to determine at least one stability metric. The condition monitoring module is configured to monitor ventilation characteristics of the flow of gas in the patient respiratory system and to provide an output indicative of the monitored ventilation characteristics. The monitored ventilation characteristics at least correspond to an occurrence of sleep disorder breathing (SDB) events in the patient respiratory system. The loop gain decision module is configured to determine a future ventilation characteristic target and plant gain target based on the determined at least one stability metric and the output from the condition monitoring module. The therapy prescription decision module is configured to determine a therapy command pressure or delivery characteristic based on the determined future ventilation characteristic and plant gain targets, wherein the therapy command pressure or delivery characteristic include a single command pressure or delivery characteristic or a combination of more than one command pressure or delivery characteristic. The pressure delivery module is configured to control the gas flow generator to deliver the flow of gas to the airway of the patient respiratory system at the determined therapy command pressure or delivery characteristic for a future breath.

In accordance with another aspect, the at least one stability metric comprises one or more of: (a) a clinical loop gain as defined by:

$$\text{loop gain} = G \cdot \frac{PACO_2 - PICO_2}{\text{lung volume}} \cdot T,$$

where G describes a dynamic responsiveness of a patient ventilation system controller, $PACO_2$-$PICO_2$ is the alveolar-inspired $PCO_2$ gradient for gas exchange, lung volume represents a volume of gas in lungs of the patient available to buffer changes in alveolar $CO_2$, T is a complex timing factor that is determined largely by circulatory delay and partly by a time constant for gas exchange in the lungs; (b) a statistical correlate to the clinical loop gain in (a), wherein the statistical correlate is generated based on breath features; and (c) a composite metric, wherein the composite metric is generated based on breath features.

In accordance with another aspect, the breath features for use in generating the statistical correlate or the composite metric of the at least one stability metric comprise one or more of: i) rate of change of minute ventilation, ii) ventilation overshoot detection, iii) ventilation undershoot detection, iv) period, phase and amplitude of periodic breathing, v) a model dealing with $CO_2$ consumption, vi) a model dealing with sleep stage and/or arousal of central nervous system, vii) simple windowed average minute ventilation, and viii) any combination of the above.

In accordance with yet another aspect, the future ventilation characteristic and plant gain targets, determined via the loop gain decision module, comprise magnitude and/or phase information of the flow of gas in the airway of the patient respiratory system. The future ventilation characteristic and plant gain targets also provide loop gain control, in response to delivery of the therapy command pressure or delivery characteristic, via the pressure delivery module. In addition, based on the magnitude and/or phase information, via opposing flow based gain, the future ventilation characteristic and plant gain targets modify, via increasing or decreasing, the loop gain for ventilation stability in the patient respiratory system.

In accordance with yet another aspect, the future ventilation characteristic and plant gain targets, determined via the loop gain decision module, render modifications to plant gain of one or more plant components of the patient respiratory system. In particular, the future ventilation characteristic and plant gain targets render modifications to plant gain via a change in one or more pressure delivery characteristic. The one or more pressure delivery characteristic can include one or more of (i) a baseline pressure, (ii) an inspiratory pressure, and (iii) an expiratory pressure.

In accordance with another aspect, the loop gain decision module further comprises a flow based gain scheduler. The flow based gain scheduler is configured to (i) schedule a flow based gain that is proportional to a magnitude and/or rate of change of a waxing and waning pattern of patient breathing effort. The flow based gain scheduler is further configured to (ii) make additions to or reductions from the patient breathing effort, thus acting in opposition of unstable waxing and waning muscle efforts in the patient respiratory system. In addition, the therapy prescription decision module is further configured to determine the therapy command pressure or delivery characteristic based upon at least a loop gain input from the flow based gain scheduler. The therapy command pressure or delivery characteristic, when delivered, is configured to generate a flow based gain that provides pressure therapy in such a manner to provide baseline pressure sufficient to overcome obstructive SDB events, or in other words, regulate plant gain and flow based gain configured to normalize loop gain.

In accordance with yet another aspect, the future ventilation characteristic target, determined via the loop gain decision module comprises a flow based pressure augmentation that is calculated continuously throughout a breath. The calculated flow based pressure augmentation is a product of (i) an instantaneous patient airway gas flow rate and (ii) a flow based gain factor. In addition, a sign of the instantaneous patient airway gas flow rate is positive during inspiration and negative during expiration. Furthermore, for a positive value of the determined flow based gain factor, the loop gain controller drives ventilation, via the pressure delivery module and the gas flow generator, to increase ventilation in the patient respiratory system. For a negative value of the determined flow based gain factor, the loop gain controller restricts ventilation, via the pressure delivery module and the gas flow generator, to decrease ventilation in the patient respiratory system.

According to yet another aspect, the loop gain decision module is further configured to determine the flow based gain factor, wherein determining the flow based gain factor includes adjusting the flow based gain factor. The determined or adjusted flow based gain factor is based on monitored conditions of the patient respiratory system in a current phase of instability of a patient breath cycle in response to the generated output signals of the at least one sensor. In addition, the loop gain decision module adjusts the flow based gain factor for a given disease state and the adjustment occurs only while conditions of the respective disease state are occurring in the patient respiratory system. In another embodiment, the condition monitoring module is further configured to collect and monitor output signals of the at least one sensor which correspond to inputs for respiratory system loop gain determination in a positive airway pressure (PAP) therapy.

In accordance with another aspect, a method for delivering a flow of gas to an airway of a patient respiratory system comprises: generating the flow of gas, generating output signals, and selectively controlling, via a loop gain controller, the flow of gas to the airway of the patient respiratory system. Generating and communicating the flow of gas to a patient circuit is accomplished via a gas flow generator, further for delivering the flow of gas to the airway of the patient respiratory system. Generating output signals related to at least one characteristic associated with the flow of gas is accomplished via at least one sensor. Selectively controlling the flow of gas to the airway of the patient respiratory system is accomplished via a loop gain controller according to a positive airway pressure (PAP) therapy mode, further in response to the generated output signals. Flow into the airway of the patient respiratory system is positive flow and flow out of the airway of the patient respiratory system is negative flow, from the gas flow generator via the patient circuit. The PAP therapy mode is configured to treat a respiratory system loop gain deficiency corresponding to a ventilation instability by utilizing loop gain for ventilation stability.

In accordance with yet another aspect, the method includes wherein selectively controlling, via the loop gain controller, comprises: (a) determining, via a stability metric module, at least one stability metric, (b) monitoring, via a condition monitoring module, ventilation characteristics of the flow of gas in the patient respiratory system and providing an output indicative of the monitored ventilation characteristics, wherein the monitored ventilation characteristics at least correspond to an occurrence of sleep disorder breathing (SDB) events in the patient respiratory system, (c) determining, via a loop gain decision module, a future ventilation characteristic target and plant gain target based on the determined at least one stability metric and the output from the condition monitoring module, (d) determining, via a therapy prescription decision module, a therapy command pressure or delivery characteristic based on the determined future ventilation characteristic and plant gain targets, wherein the therapy command pressure or delivery characteristic include as single command pressure or delivery characteristic or a combination of more than one command pressure or delivery characteristic, and (e) controlling, via a pressure delivery module, the gas flow generator to deliver the flow of gas to the airway of the patient respiratory system at the therapy command pressure or delivery characteristic for a future breath.

According to a further aspect, the at least one stability metric comprises one or more of: (a) a clinical loop gain as defined by $$\text{loop gain} = G \cdot \frac{PACO_2 - PICO_2}{\text{lung volume}} \cdot T,$$

where G describes a dynamic responsiveness of a patient ventilation system controller, $PACO_2$-$PICO_2$ is the alveolar-inspired $PCO_2$ gradient for gas exchange, lung volume represents a volume of gas in lungs of the patient available to buffer changes in alveolar $CO_2$, T is a complex timing factor that is determined largely by circulatory delay and partly by a time constant for gas exchange in the lungs; (b) a statistical correlate to the clinical loop gain in (a), wherein the statistical correlate is generated based on breath features; and (c) a composite metric, wherein the composite metric is generated based on breath features.

In accordance with yet another aspect, the method includes wherein the breath features for use in generating the statistical correlate or the composite metric of the at least one stability metric comprise one or more of: i) rate of change of minute ventilation, ii) ventilation overshoot detection, iii) ventilation undershoot detection, iv) period, phase and amplitude of periodic breathing, v) a model dealing with $CO_2$ consumption, vi) a model dealing with sleep stage and/or arousal of central nervous system, vii) simple windowed average minute ventilation, and viii) any combination of the above.

According to yet another aspect, the method includes wherein the future ventilation characteristic and plant gain targets, determined via the loop gain decision module, (i) comprise magnitude and/or phase information of the flow of gas in the airway of the patient respiratory system, (ii) provide loop gain control, in response to delivery of the therapy command pressure or delivery characteristic, via the pressure delivery module, and (iii) based on the magnitude and/or phase information, via opposing flow based gain, modify, via increasing or decreasing, the loop gain for ventilation stability in the patient respiratory system. In addition, the future ventilation characteristic and plant gain targets, determined via the loop gain decision module, render modifications to plant gain of one or more plant components of the patient respiratory system via a change in one or more pressure delivery characteristic. The one or more pressure delivery characteristic includes one or more of (i) a baseline pressure, (ii) an inspiratory pressure, and (iii) an expiratory pressure.

According to another aspect, the method includes wherein selectively controlling, via the loop gain controller, further comprises: (c)(i) scheduling, via a flow based gain scheduler of the loop gain decision module, a flow based gain that is proportional to a magnitude and/or rate of change of a waxing and waning pattern of patient breathing effort, and (c)(ii) making additions to or reductions from the patient breathing effort, via the determined future ventilation characteristic target and plant gain target, thus acting in opposition of unstable waxing and waning muscle efforts in the patient respiratory system. In a further embodiment, the method includes wherein selectively controlling, via the loop gain controller, further comprises: (d)(i) determining, via the therapy prescription decision module, the therapy command pressure or delivery characteristic based upon at least a loop gain input from the flow based gain scheduler, wherein the therapy command pressure or delivery characteristic, when delivered, is configured to generate a flow based gain that provides pressure therapy in such a manner to provide baseline pressure sufficient to overcome obstructive SDB events, or in other words, regulate plant gain and flow based gain configured to normalize loop gain.

The embodiments of the present disclosure advantageously treat an instability (i.e., instability in the respiratory or ventilation system) of a breathing patient using positive pressure therapy and a negative feedback closed loop control system which modulates human respiratory system loop gain (i.e., ventilation system loop gain) to counter act swings in patient ventilation response to a given PAP therapy or treatment. Additional advantages provided via the embodiments of the present disclosure include one or more of the following: 1) use of flow based gain to counter act the spontaneous effort, this does result in a pressure but that pressure is proportional to the spontaneous flow; 2) use of plant gain as an adjunct method to provide loop gain stability (e.g., if the patient is un-stable in his/her response to a given PAP therapy or treatment, the first line of defense might be to increase the EPAP pressure to increase the plant gain); and 3) previous known ASV devices use long observation windows, with a target determined by the a proportion of the computed average, whereas the algorithm according to the present embodiments uses a stability metric which may be computed over a shorter time window.

Still further advantages and benefits will become apparent to those of ordinary skill in the art upon reading and understanding the following detailed description.

BRIEF DESCRIPTION OF THE DRAWINGS

The embodiments of the present disclosure may take form in various components and arrangements of components, and in various steps and arrangements of steps.

Accordingly, the drawings are for purposes of illustrating the various embodiments and are not to be construed as limiting the embodiments. In the drawing figures, like reference numerals refer to like elements. In addition, it is to be noted that the figures may not be drawn to scale.

DETAILED DESCRIPTION

Figure 1:
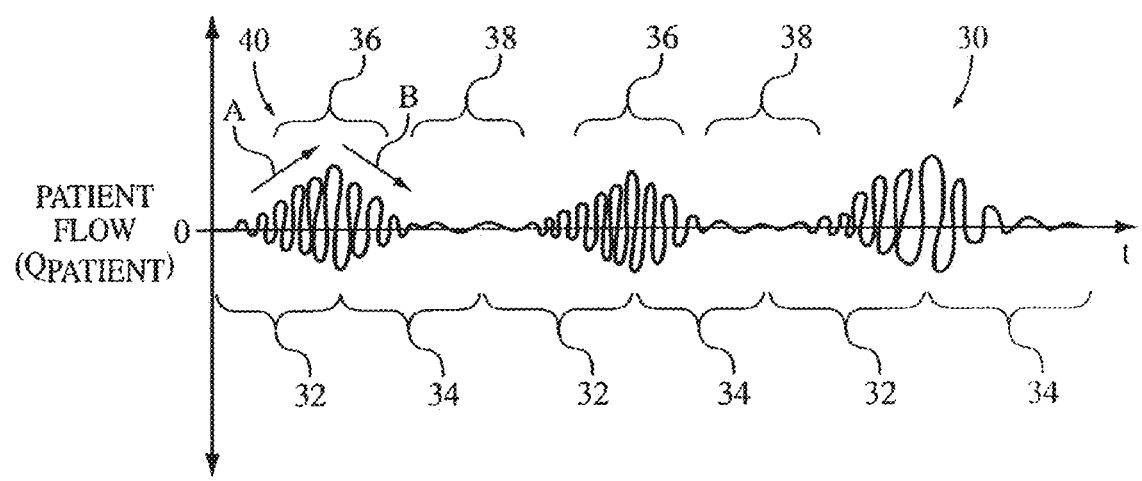
FIG. 1 is a graphical view representation of a typical Cheyne-Stokes respiratory cycle that is treated by a system and method for positive airway pressure therapy utilizing loop gain for ventilation stability according to the embodiments of the present disclosure.

The embodiments of the present disclosure and the various features and advantageous details thereof are explained more fully with reference to the non-limiting examples that are described and/or illustrated in the drawings and detailed in the following description. It should be noted that the features illustrated in the drawings are not necessarily drawn to scale, and features of one embodiment may be employed with other embodiments as the skilled artisan would recognize, even if not explicitly stated herein. Descriptions of well-known components and processing techniques may be omitted so as to not unnecessarily obscure the embodiments of the present disclosure. The examples used herein are intended merely to facilitate an understanding of ways in which the embodiments of the present may be practiced and to further enable those of skill in the art to practice the same. Accordingly, the examples herein should not be construed as limiting the scope of the embodiments of the present disclosure, which is defined solely by the appended claims and applicable law.

It is understood that the embodiments of the present disclosure are not limited to the particular methodology, protocols, devices, apparatus, materials, applications, etc., described herein, as these may vary. It is also to be understood that the terminology used herein is used for the purpose of describing particular embodiments only, and is not intended to be limiting in scope of the embodiments as claimed. It must be noted that as used herein and in the appended claims, the singular forms "a," "an," and "the" include plural reference unless the context clearly dictates otherwise.

Unless defined otherwise, all technical and scientific terms used herein have the same meanings as commonly understood by one of ordinary skill in the art to which the embodiments of the present disclosure belong. Preferred methods, devices, and materials are described, although any methods and materials similar or equivalent to those described herein can be used in the practice or testing of the embodiments.

According to one embodiment, positive airway pressure (PAP) is used to treat a number of sleep disordered breathing conditions for a human respiratory system (or ventilation system) including obstructive sleep apnea (OSA) and Cheyne-Stokes respiration (CSR). In addition, loopgain (or "loop gain"), as discussed herein, describes a magnitude of ventilation response of the ventilation system to disturbances in that system. Underdamped systems with a loopgain greater than one (i.e., loopgain>1, also referred to herein as "high loopgain") are unstable and lead to repetitive hypopneas in OSA and CSR breathing. Current known auto-servo ventilation (ASV) devices provide patient ventilation when needed to increase ventilation; however, such current known ASV devices are not capable of restricting patient ventilation when patient ventilation response (e.g., muscle effort) exceeds a baseline. In other words, the current known ASV devices attempt to stabilize ventilation by providing support when necessary to ensure a ventilation target determined as a proportion of the spontaneous ventilation. This provides a limited benefit because that method fails to recognize the waxing and waning time variant of respiratory drive. In contrast, the embodiments of the present disclosure advantageously monitor for the time varying effort and provide opposing ventilation in phase with the central controller.

According to one aspect, the embodiments of the present disclosure advantageously address the inability in prior known ASV devices to treat the hyperventilation phase in high loop gain patients. In particular, the embodiments of the present disclosure advantageously treat an instability (i.e., instability in the respiratory or ventilation system) of a breathing patient using positive pressure therapy and a negative feedback closed loop control system which modulates human respiratory system loop gain (i.e., ventilation system loop gain) to counter act swings in patient ventilation response.

While a comprehensive mathematical model for the human respiratory system (or ventilation system) is not needed, the major components of the human respiratory system and their contribution to ventilation stability are described. Lumped models allow for generalization, a widely accepted methodology which allows a topic to be discussed in broad terms. For example, it is acceptable to frame out a problem without defining each and every component, especially if their contribution is small and less relevant or non-linear and complex. For the purpose of this disclosure, the following respiratory system component descriptions for central controller, plant, plant gain and plant gain modification, body compensatory modifiers, and clinician plant component gain modification, will be used.

Central Controller: Central control of ventilation in the human respiratory system takes place within the medulla and pons of the brain, utilizing both central and peripheral chemoreceptors. The medulla is a section of the brain located in the brainstem which is responsible for automatic functions like breathing, blood pressure, circulation and heart functions, and digestion. The pons is a horse shoe-shaped structure in the brain stem of the brain that is crucial to life. The pons consists of nerve fibers that connect the cerebrum and the cerebellum, and bridges sensory information between the left and right hemispheres of the brain. Central chemoreceptors monitor $CO_2$ levels in the cerebrospinal fluid, while peripheral chemoreceptors located in aortic and carotid bodies monitor $CO_2$ and $O_2$ in the blood. The aortic body is located along the aortic arch. The carotid body is in the carotid artery. Due to location, the time constant of central chemoreceptors is very slow (i.e., around 50 seconds) relative to peripheral chemoreceptors with a time constant between 10 and 30 seconds.

Plant: The human respiratory or ventilation system plant is comprised of plant components. As discussed herein, the lumped plant model includes at least the lungs, gas exchange units (i.e., the alveoli), and gas transport units (i.e., hemoglobin). In addition, the plant has an overall plant gain corresponding to a relationship between plant input and plant output.

Plant Gain and Plant Gain Modification: Each plant component has its own gain, the relationship between input and output. Those gains are non-linear, differ between individuals and contribute to the overall plant gain. The ventilation plant is a complex interaction of dynamic plant components. For instance, the plant gain of the lungs is constantly changing by air mixing, lung volume, heart rate, interstitial fluid, body position, etc. To assist in further understanding, several examples of constantly changing contributions to plant gain are presented herein below, including V/Q ratio and circulation delay.

V/Q ratio is an expression of an operational efficiency of the alveoli in the lungs and expresses a number of Units of Ventilation at the alveoli to a number of Gas Exchange units in the blood. V/Q efficiency is modified on the ventilated side of the alveoli by the magnitude of partial pressures of oxygen ($O_2$) and carbon dioxide ($CO_2$). For each breath, the depth of breath and breathing rate, as well as Functional Residual Capacity (FRC) which is the volume of air present in the lungs at the end of passive expiration, will have an impact on the partial pressure of gases present at the alveoli. Positive lung pressure impacts V/Q by opening small airways and allowing for increased ventilation to distal alveoli. Heart rate and cardiac output also impact the perfusion efficiency as well as the gas exchange process, the latter of which is dependent on the movement of hemoglobin across the alveoli. Because the lung is a complex pulmonary vascular network, depth of breath and interstitial fluid level will also play a role in V/Q efficiency.

Another contribution to plant gain is circulation delay, in which cardiac output can contribute a cycle length in periodic breathing. The time delay for newly perfused blood to reach the chemo receptors is a function of the efficiency of the heart (e.g., as relating to ejection fraction, cardiac output, vascular resistance, and circulation volume). It is generally accepted that loop delay contributes to the likelihood of Cheyne-Stokes breathing in patients suffering with Chronic Heart Failure with low left ventricle ejection fraction (LVEF) (e.g., 20%-50%). It is also generally accepted that the cycle length of periodic breathing is related to the LVEF with longer cycle times being associated with more impaired LVEF. By comparison, the cycle time observed in treatment emergent periodic breathing is 30 seconds relative to low LVEF (<20%) cycle times approaching 86 seconds, for example. In addition to the above, other plant gain modifiers can include heart rate, circulating blood volume, and hemoglobin levels, which are not further discussed herein.

Bodies Compensatory Modifiers: Some plant components act in a compensatory manor to compensate for another plant that is compromised (i.e., a compromised plant). Several examples will now be discussed. One of the easiest examples of this is the heart rate response to poor ventilation. The heart rate can be seen increasing in obstructive sleep apnea (OSA) subjects to maintain adequate oxygen levels in the tissues during low ventilation periods. In this example, low ventilation is a reduction in plant gain, while increased heart rate is an increase in plant gain.

A second example of a plant component acting in a compensatory manor to compensate for another compromised plant is chemosensitivity in central sleep apnea (Chemosensitivity In CSA). In this example, central chemosensitivity is a response by the central controller to compensate for reduced cardiac output. Patients with chronic heart failure have a compromised cardiac output which creates a loop delay in circulation time. The time delay between gas exchange in the lungs and the blood reaching the chemo sensors is longer than normal. Loop delay can be viewed as a reduction in plant gain, while a compensatory response to this condition by the central controller is the increased chemosensitivity to $CO_2$ which can be viewed as an increase in plant gain.

Increased chemosensitivity is sufficient to maintain stable ventilation in early stages of CO impairment and deep sleep. As the CO impairment worsens, ventilation instability ensues due to total loop gain approaching one (1). This condition has been described as a waxing and waning breathing pattern, periodic breathing, Cheyne-Stokes Respiration (CSR) and Hunter Cheyne-Stokes Breathing. The cycle time of periodic breathing has been correlated to the left ventricle ejection fraction (LVEF) with a range between 60 and 90 seconds.

Treatment emergent periodic breathing occurs in approximately 5 to 15 percent otherwise healthy, non-cardiac impaired patients during initial exposure to positive airway pressure. In these patients, exposure to positive airway pressure increases ventilated airways, gas exchange and loop gain, thereby creating unstable periodic breathing identical to CSR except with a cycle time of 30 seconds. This condition normally diminishes over time; however, a small percentage of patients require therapeutic interventions similar to the CSR patients.

A third example of a plant component acting in a compensatory manor to compensate for another compromised plant is chemosensitivity in obstructive sleep apnea (Chemosensitivity In OSA). Chemosensitivity and high loop gain have also been used to describe sleep disordered breathing in OSA. In addition, high loop gain has been used to describe intermittent hypoxia mixed events in OSA subjects. In these centrally mediated hypopneas, patients exhibit ventilation overshoot resulting in repetitive cycles of hyperventilation, reduced upper airway muscle dilation and partial to complete closure of the upper airway. The ventilatory response to hypoxia is often underdamped, leading to overshoot in ventilation and hypocapnea. While continuous positive airway pressure CPAP is the primary therapeutic intervention for airway collapse, CPAP increases plant gain and can further promote loop gain. This sometimes leads to over titration of CPAP pressure until loop gain is inhibited by excessively high expiratory positive airway pressure (EPAP) pressures.

Clinician Plant Component Gain Modification: Clinicians have sought interventions to improve ventilation stability in patients with impaired loop gain by altering the gain of plant components. For chronic heart failure, when patients have ventilation instability due to hyper chemosenstivity, the treatment strategy is to increase the gain of a plant component by way of a plant component modification. This will in affect reduce the operational burden on the central controller of the human respiratory system, which in turn will allow for a reduction in its responsiveness to $CO_2$ and $O_2$ signals. Some strategies target the impaired cardiac muscle with inotropic drugs which increase the contractility of the heart.

In addition, positive pressure CPAP (continuous positive airway pressure) therapy in acute care has been used to improve cardiac output. Positive pressure increases plant gains by increasing ventilated space, reducing venous return and increasing cardiac output by way of reduced ventricular volume described by the Frank-Starling mechanism. Diuretics act in a similar manner to alter plant gain by managing blood volumes. Inhaled oxygen increases lung component gain by increasing perfusion efficiency. Inhaled $CO_2$ raises carbon dioxide pressure ($PCO_2$), acetazolamide lowers alveolar carbon dioxide pressure ($PACO_2$), both reduce the inspired carbon dioxide pressure ($PICO_2$) gradient. Body position to lateral or upright positions will increase lung volume and its contribution to overall system loop gain.

System Loop Gain: Overall system loop gain is the system responsiveness to a disturbance. In a negative feedback system, the loop gain is the product of controller and plant gains against the observed error signal from the central and peripheral chemo receptors. In particular, loop gain of the ventilatory control system (i.e., of the human respiratory system) can be quantified in terms of four measurable factors, according to the relationship given in Equation 1.

$$\text{loop gain} = G \cdot \frac{PACO_2 - PICO_2}{\text{lung volume}} \cdot T \qquad \text{Eq. 1}$$

where G describes the dynamic responsiveness of the controller (peripheral and central chemoreceptor sensitivity) of the human respiratory system. The remaining factors make up the gain due to the plant: $PACO_2$-$PICO_2$ is the alveolar-inspired $PCO_2$ gradient for gas exchange (it is noted that plant gain would be zero if alveolar and inspired levels were equal); lung volume represents the volume of gas in the lungs available to buffer changes in alveolar $CO_2$; T is a complex timing factor that is determined largely by the circulatory delay and partly by the time constant for gas exchange in the lungs (formally, $T=[(2\pi/[\text{cycle period}])^2 + 1/\tau_{lung2}]^{-0.5}$). An almost identical equation can be written to describe the additive contribution to loop gain via the feedback control of $O_2$. Since controller gain (describes the change in ventilation of the human respiratory system in response to changes in $PCO_2$ (or $PO_2$), G can be modified by additional factors. During the CSA cycle, as ventilatory drive rises there is often an accompanying progression from sleep to wake that further augments ventilatory drive, and in turn further increases the swing in ventilation and raises G. In addition, changes in upper airway patency that occur in parallel with $PCO_2$ in patients with a responsive upper airway will also raise G.

Figure 2:
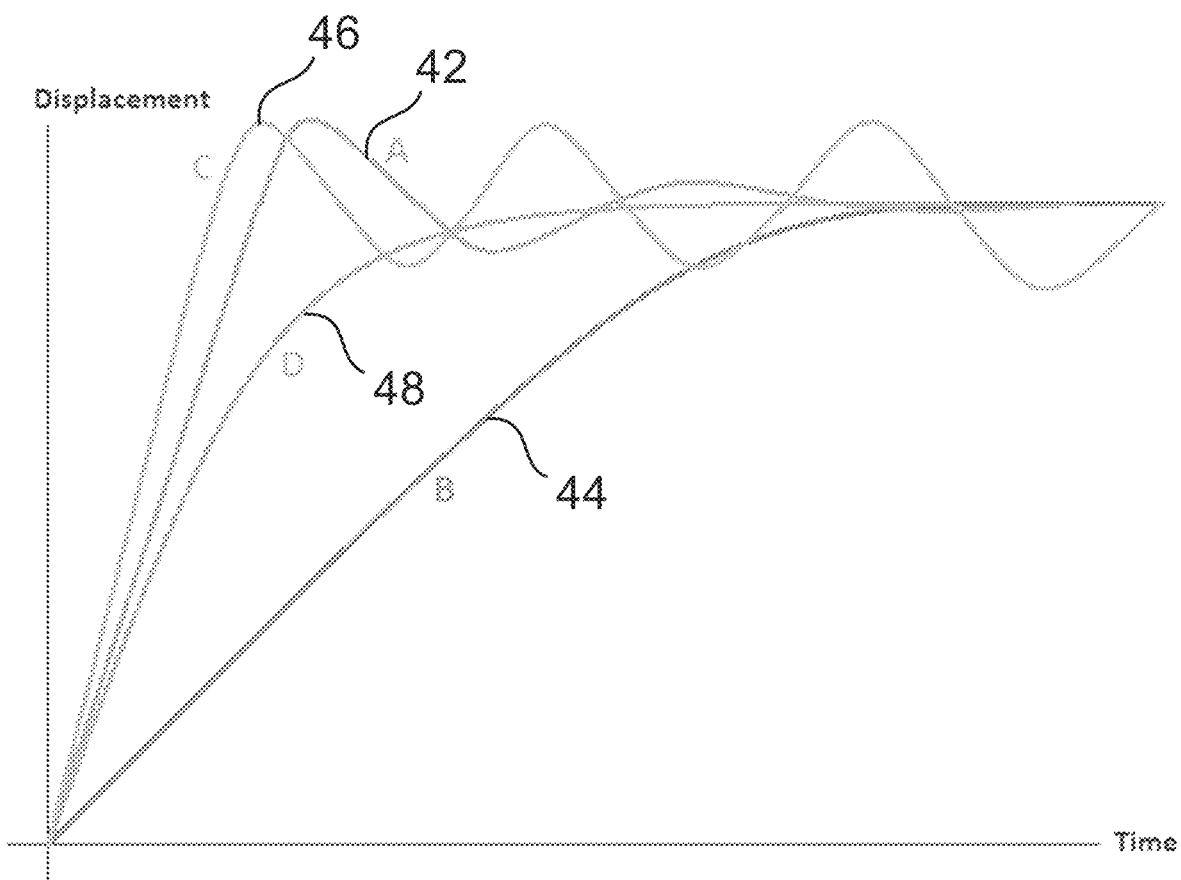
FIG. 2 is a graphical view representation of several responses of a control system versus time that are categorized into under damped, critically damped and overdamped.

Clinical Importance of Loop Gain: Loop gain becomes clinically relevant in patients when control of ventilation is compromised due to low loop gain or high loop gain instability. It has been determined that system loop gain exceeds one (1) (i.e., the system becomes unstable) only in specific circumstances. Loop gain can be further understood in terms of general control theory, as follows. The response of a control system can be categorized into the categories of underdamped, critically damped and overdamped. With reference now to FIG. 2, four control system responses, labeled A (42), B (44), C (46) and D (48), are illustrated. The system responses A, B, and D have a loop gain less than 1, contrasted by the system response C which represents a loop gain greater than 1. In FIG. 2, the response curve A represents an underdamped response. The response curve B represents an overdamped response. The response curve C represents a non-settling underdamped condition with a loop gain greater than 1. Lastly, the response curve D represents a critically damped condition.

Measuring Loop Gain: There are several methods by which loop gain has been measured in both wake and sleeping patients. Wake testing methods have measured loop gain through a single or series of breath holds. Sleeping patients have undergone CPAP drop tests where differences in plant gain are driven through a reduction in CPAP pressure, corresponding differences in both ventilation and effort are collected and these difference values are used to estimate loop gain. That testing has produced models which have been further used to estimate loop gain from polysomnography (PSG) data without interventional procedures.

Unfortunately, these methods produce loop gain values which are subject to the conditions by which a respective loop gain value was determined and the value of loop gain has to be constructed at a particular frequency, which may be different than the fundamental frequency of a particular patient. Additionally, for a given patient, loop gain is not a constant but will vary based on sleep stage, body position, therapeutic pressure levels.

The clinical application of loop gain: In practice, the clinical use of loop gain may aid the clinician in the provision of personalized care. Loop gain may help validate the clinician's intuition for the type of therapeutic intervention. Protocols and guidelines are far from established, but likely baseline conditions would be collected including metrics from the area of respiratory science. These metrics include apnea hypopnea index (AHI), arousal indices, sleep continuity metrics, blood gases, desaturation indices, etc. Loop gain and/or some ventilation stability metrics which correlate to loop gain may be more generally applied across populations. This baseline data would be interpreted and interventions would then be introduced based on the interpretation.

Ideally interventions would be self-titrating against a set of goals. Those goals could be multifactorial to stabilize breathing and/or treat underlying conditions such as obstructive sleep apnea. For example, CPAP benefits loop gain by increasing the plant gain which in turn reduces the load on the central controller of the human respiratory system. In a multifactorial titration, the intervention examines the benefit to both obstructive sleep apnea events as well as benefits to loop gain. CPAP pressure may be increased until (i) either no further benefit is observed in either outcome or (ii) negative impact is observed in either outcome. Without this approach, and focusing solely on the elimination of events, it is possible to increase plant gain causing loop gain instability.

Post treatment assessment of stability and co-treatment goals could be assessed. Regular follow up, especially in some automatic means, would allow the clinician to make adjustments as needed.

As positive airway pressure therapy has evolved, there appears a trend towards precision medicine, or disease specific medicine. A brief review of existing PAP therapy algorithms is contained in Table 1 presented herein below. As will be described, each one of the existing PAP therapy algorithms has been designed with targeted goals. In many cases, the pressure delivery is personalized to the individual throughout the therapy session.

TABLE 1

| ID | Sub Therapy | Abbreviation | Disease State | Control Metric | Breathing Phase |
|---|---|---|---|---|---|
| 1 | Flow Based Gain Therapy | FBGT | Ventilation Instability | Flow based pressure augmentation | Throughout |
| 2 | Automatic Continuous Positive Airway Pressure | Auto CPAP | Obstructed Sleep Apnea | Expiration Pressure | Throughout |

TABLE 1-continued

| ID | Sub Therapy | Abbreviation | Disease State | Control Metric | Breathing Phase |
|----|-------------|--------------|---------------|----------------|-----------------|
| 3 | Auto Servo Ventilation | ASV | Periodic breathing | Expiratory Pressure, Pressure Support | Expiration (ASVe) Inspiration (ASVi) |
| 4 | Average Volume Assured Ventilation | AVAPS | Lung disease, obesity hypoventilation syndrome | PS minimum | Inspiration |
| 5 | Flex | Cflex, BiFlex | comfort | Flow based pressure augmentation | Expiration |
| 6 | Airflow Comfort | AC | comfort | Flow based pressure augmentation | Throughout |
| 7 | Otis Work of Breathing | Otis | comfort | Pressure Support For Work Of breathing | Inspiration |

With respect to CPAP Therapy Design and its common design element, the basic positive airway pressure device contains a pneumatic source such as a rotating fan, a pressure sensor for closed loop fan control and a pneumotachograph to measure airflow. The patient (or subject receiving treatment) is connected by a flexible conduit and a mask with a deliberate orifice to allow for exhaust of $CO_2$. Using the pressure sensor as feedback, the fan speed is adjusted to a desired mask pressure which includes pressure drops for conduit and mask determined by current flow conditions. Small residual flow-based control errors may affect patient loop gain as the mask pressure varies due to pressure control dynamics.

In addition to the above discussion, a brief review of several therapies indicated in Table 1 is provided herein below.

Continuous Positive Airway Pressure (CPAP) therapy is primarily used for obstructive sleep apnea but can also be used to treat acute cardiogenic pulmonary edema.

BiLevel Pressure (BiPAP) therapy provides alternating high and low pressure to drive ventilation during inspiration. This therapy mode is primarily used in patients with resistive, restrictive lung disease and obesity hypoventilation patients. BiPAP delivers consistent pressure support regardless of patient effort. The resulting tidal volumes will vary and depending on the amount of pressure support configured, the patient may be left with no control in the inspired tidal volume, which can be destabilizing to high loop gain patients and is likely to cause hypocapnea. BiPAP can be configured to deliver machine initiated or timed breaths when patient effort is absent or reduced due to hypocapnea.

Average Volume Assured Pressure Support (AVAPS) therapy is a therapy mode that uses the benefits of BiPAP with a closed loop control around a tidal volume setpoint. This mode is beneficial to BiPAP patients with the added benefit of downregulating pressure support in accordance with patient muscle effort. AVAPS can also support machine breaths.

Proportional Assist Ventilation (PAV) is a therapy mode that is implemented by monitoring the instantaneous patient flow rate $\dot{V}$ and volume (V) and computes an applied pressure (P) according to the equation of motion $P=f1(V)+f2(\dot{V})$, where f1 and f2 are appropriately selected functions for the relation between pressure and volume (elastic assist) and pressure and flow (resistive assist).

Auto Servo Ventilation (ASV) is a therapy mode designed to treat patients with high loop gain ventilation control deficiencies. The ASV device monitors some aspect of ventilation and provides pressure support only as needed to maintain some proportion of that value (typically 90% of monitored value). Because of that proportion, the ASV device design allows the patient to guide the therapy. Similar to BiPAP, machine breaths can be configured in this mode.

Various problems and/or disadvantages are overcome by the positive airway pressure therapy system utilizing loop gain for ventilation stability according to the embodiments of the present disclosure, further as can be understood via the discussion herein.

Referring again to Table 1 above, Auto Servo Ventilation is described as a therapy designed to treat high loop gain disease states. Existing auto servo devices monitor some aspect of ventilation over several minutes, compute some proportion of that value and provide pressure support as needed to ensure that future ventilation is at least of that magnitude. These ventilation targets are some measurement of magnitude of ventilation such as tidal volume, minute ventilation or peak flow. However, there are several disadvantages of this current technology in need of improvement. The current ASV devices only provide pressure support during a period of time when a reduction in breathing (hypopnea) occurs. The pressure support provided via the current ASV devices is only capable of driving more ventilation to the patient. During the hyperpnea (i.e., increase in ventilation), the current ASV device reverts to a pressure pattern equivalent to CPAP which is essentially non-therapeutic in terms of reducing the waxing and waning breathing pattern.

The deficiency discussed in the immediately previous paragraph was addressed in U.S. Pat. No. 9,463,293, entitled "SERVO VENTILATION USING NEGATIVE PRESSURE SUPPORT," and U.S. Pat. No. 9,044,560, entitled "SERVO VENTILATION USING PRESSURE DROP FROM BASELINE." In these two patents, a method is described which includes reducing ventilation whenever muscle effort exceeds baseline. These approaches continue to target some magnitude of ventilation, increasing pressure support whenever muscle effort falls below baseline, and increasing pressure support whenever muscle effort exceeds baseline. While these approaches offer the ability of a servo device to treat an overventilation aspect of therapy control, they do not provide a targeted therapy specific to loop gain deficiency.

Accordingly, the embodiments of the present disclosure advantageously provide a positive airway pressure (PAP) therapy algorithm which treats loop gain deficiency with an approach targeted towards the root cause of this deficiency.

In addition to definitions provided herein above, the following additional definitions shall apply with respect to the embodiments of the present disclosure:

Loopgain (or "loop gain"): The formal diagnostic assessment of respiratory loopgain is well established in the clinical community. Some of those assessment methods involve conducting laboratory tests while other less invasive methods have been described using information from polysomnography (PSG). In central sleep apnea (CSA) and treatment emergent periodic breathing, loopgain patients exhibit a cyclic respiratory pattern which mathematically is described well in frequency domain mathematics. In obstructive sleep apnea (OSA), the over ventilation response to an obstructive event requires different analysis methods. For the description of this work, recognizing that there will not be a single form of representation, the term loopgain will be used as a general term, non-specific to any specific algorithm or method of loopgain determination. For this discussion, loopgain may be any form of descriptive representation of ventilation stability including but not limited to existing known published forms of loopgain, time constants of response, rate of change metrics, slew rate, overshoot measurements, sleep stage, arousals, etc. Additionally, artificial intelligence can be utilized to construct a model representing loopgain as a composite metric.

Flow Based Gain Therapy (FBGT) is a general term that may incorporate one or more combination of specific means to alter device PAP therapy interaction with the patient. As discussed above with reference to U.S. Pat. No. 9,463,293, entitled "SERVO VENTILATION USING NEGATIVE PRESSURE SUPPORT," and U.S. Pat. No. 9,044,560, entitled "SERVO VENTILATION USING PRESSURE DROP FROM BASELINE," it is possible to oppose muscle effort and reduce the effective ventilation in a patient utilizing negative pressure support. In contrast to the mentioned patent references, for the embodiments of the present disclosure, the system and method make use of a flow based gain (or flow based gain factor) capability by which a portion of the supported mask pressure is computed as a gain factor multiplied by the instantaneous patient flow rate. The gain factor (i) when positive, would drive ventilation and, (ii) when negative, would restrict ventilation. While the application of a patient flow based gain may appear to be similar to the Proportional Assist Ventilation (PAV) equation (as discussed further herein), there are clear differences in intent. PAV incorporates a flow based gain factor to overcome respiratory impedance. In the therapy according to the system and method embodiments of the present disclosure, the flow based gain (or flow based gain factor) is altered to manage ventilation stability, including the application of negative gain to counteract muscle effort. Flow based ventilation gain therapy acts as a control stabilizer for the central controller of the human respiratory system.

The system and method embodiments of positive airway pressure therapy utilizing loop gain for ventilation stability of the present disclosure advantageously address the role of chemosensitivity in CSA patients. For CSA and treatment emergent periodic breathing, during waxing and waning breathing patterns, the system includes a gain scheduler, configured to schedule a flow based gain that is proportional to the magnitude and/or rate of change of the waxing and waning pattern, makes additions to or reductions from patient effort, thus acting in opposition to the unstable muscle efforts of the patient. In doing so, the PAP therapy utilizing loop gain for ventilation stability provides more normalized ventilation and entrains the central controller of the human respiratory system into a stable breathing pattern.

The system and method embodiments of positive airway pressure therapy utilizing loop gain for ventilation stability of the present disclosure also advantageously address the role of chemosensitivity in OSA patients. Obstructed sleep apnea patients with chemosensitivity will also benefit from the PAP therapy utilizing loop gain for ventilation stability. During obstructive events, as a result of an arousal response to hypoxemia, large swings in ventilation occur. This therapy (i.e., utilizing loop gain for ventilation stability) provides a similar benefit to the patient via flow based gain scheduling. In such a case for the patient, most obstructive events are prevented by not allowing muscle effort to cause swings in minute ventilation sufficient to allow this undesirable pattern to begin.

The positive airway pressure therapy system utilizing loop gain for ventilation stability, according to the embodiments of the present disclosure, includes system components for performing at least one sub-therapy, e.g., flow based gain therapy (FBGT). As discussed, FBGT involves several sub-processes which include monitoring of conditions, determination of response, delivery of therapy, and reporting of information. A brief discussion of each of the sub-processes is provided below.

With respect to monitoring of conditions and generation of a flow based gain factor (or flow based gain value), the system and method are based upon and/or incorporate the following. The foundation for loopgain control is a flow based gain factor which offsets the actions of the central controller of the human respiratory system. In high loopgain chemosenstivity patients, the central controller is over responding to chemical stimulus from the chemo sensors. The goal of the FBGT is to prevent the over and/or under compensation of the central controller with the use of pressure support acting against and/or with the action of the diaphragm to prevent and/or assist ventilation during the unstable condition. Throughout the breath, the flow based pressure augmentation is calculated as the product of patient flow rate and the flow based (FB) gain factor, as per the following expression:

$$\text{FB pressure augmentation} = (\text{Patient Flow Rate}) \times (\text{FB gain value}).$$

It is important to understand that the calculation for this FB pressure augmentation occurs continuously throughout the breath. The sign of the patient flow rate is positive during inspiration and negative during expiration. If the FB gain factor is positive, the result will be increased ventilation. Conversely, if the FB gain factor is negative, the result will be decreased ventilation. The following section will now discuss how this FB gain factor is determined, which is followed by a discussion on how this gain factor is applied.

There are several forms of instability that the design of a FBGT may consider. In a first example, consider a CSA patient who is exhibiting periodic breathing (i.e., waxing and waning). The FB gain factor may be updated based on the current phase of that cycle, moving in opposing form to the cycling ventilation. In this manor, the gain factor is configured to directly oppose the central controller of the human respiratory system. Consider next a patient that is exhibiting acute sleep disordered breathing (SDB) events with overshoot and undershoot. In this case, the FB gain (or FB gain factor) may be adjusted to become active only during those periods of acute SDB events. In this example, gain would be adjusted to become negative during ventilation overshoot and positive during ventilation undershoot. Additional examples of disease states include Obesity Hypoventilation Syndrome and Respiratory Event Related Arousals, wherein the gain adjustment is particular to the disease state and occurs only while the conditions of the respective disease state are occurring.

Artificial intelligence (AI) may be employed to generate a comprehensive model of loop gain using a multivariate approach with ventilation metrics. The ventilation metrics may include one or more common respiratory parameters such as tidal volumes, minute ventilation, and sleep disordered breathing events. The ventilation metrics could also include time windowing, and/or statistical processing for minimum, maximum, and standard deviation. Machine learning (ml) may be employed to generate a model or function which is useful for predicting or determining loop gain, given one or more independent variables, which may include ventilation metrics and/or features. One benefit of this approach is that the machine learning model may be computationally inexpensive relative to the target computation. The multivariate result may also be more generalized across- or limited to certain-populations and circumstances. Machine learning techniques include multi regression linear and neural networks.

The foundation of FBGT, in the positive airway pressure therapy system utilizing loop gain for ventilation stability according to the embodiments of the present disclosure, resides in the calculation of at least one model containing at least one metric describing ventilation stability; however, it is understood this could be a multitude of models containing a multitude of metrics (i.e., stability metrics). For example, the at least one model or the multitude of models may be generated by one or more of AI, ml, or a combination of AI and ml. Several embodiments for the stability metric can include one or more of the following:

a) a clinical loop gain as defined in the current literature (e.g., Equation 1 disclosed herein may be used);
b) a statistical correlate to the clinical loop gain in (A), wherein the statistical correlate is generated using features discussed further herein below; and
c) a composite metric that is generated using features discussed herein below.

As can be readily understood, various features may be used to define respiratory stability. In particular, there are a number of breath features that would aid in the construction of a stability metric, including, but not limited to:

i) rate of change of minute ventilation,
ii) ventilation overshoot detection,
iii) ventilation undershoot detection,
iv) period, phase and amplitude of periodic breathing,
v) a model dealing with $CO_2$ consumption,
vi) a model dealing with sleep stage and/or arousal of central nervous system,
vii) simple windowed average minute ventilation, and
viii) any combination of the above.

The output of the FBGT, in the positive airway pressure therapy system utilizing loop gain for ventilation stability according to the embodiments of the present disclosure, is a gain factor scaled appropriately to provide pressure support in opposing form to the patient's muscle effort driving ventilation. Once the FB gain factor is determined, it becomes part of the FBGT therapy subsystem, according to the embodiments of the present disclosure.

In one embodiment, the system and method generate a 4-minute moving window of minute ventilation. The gain factor is determined by subtracting the 4-minute average from the 3-breath average minute ventilation. This difference is then multiplied by a scaling factor, typically a value between 0.01 and 0.09, and more preferably a value of 0.07 as a recommendation. In other words, the gain factor is determined as per the following expression:

FB Gain Factor=(4 minute avg min vent−3 breath avg min vent)×(scaling factor).

Figure 3:
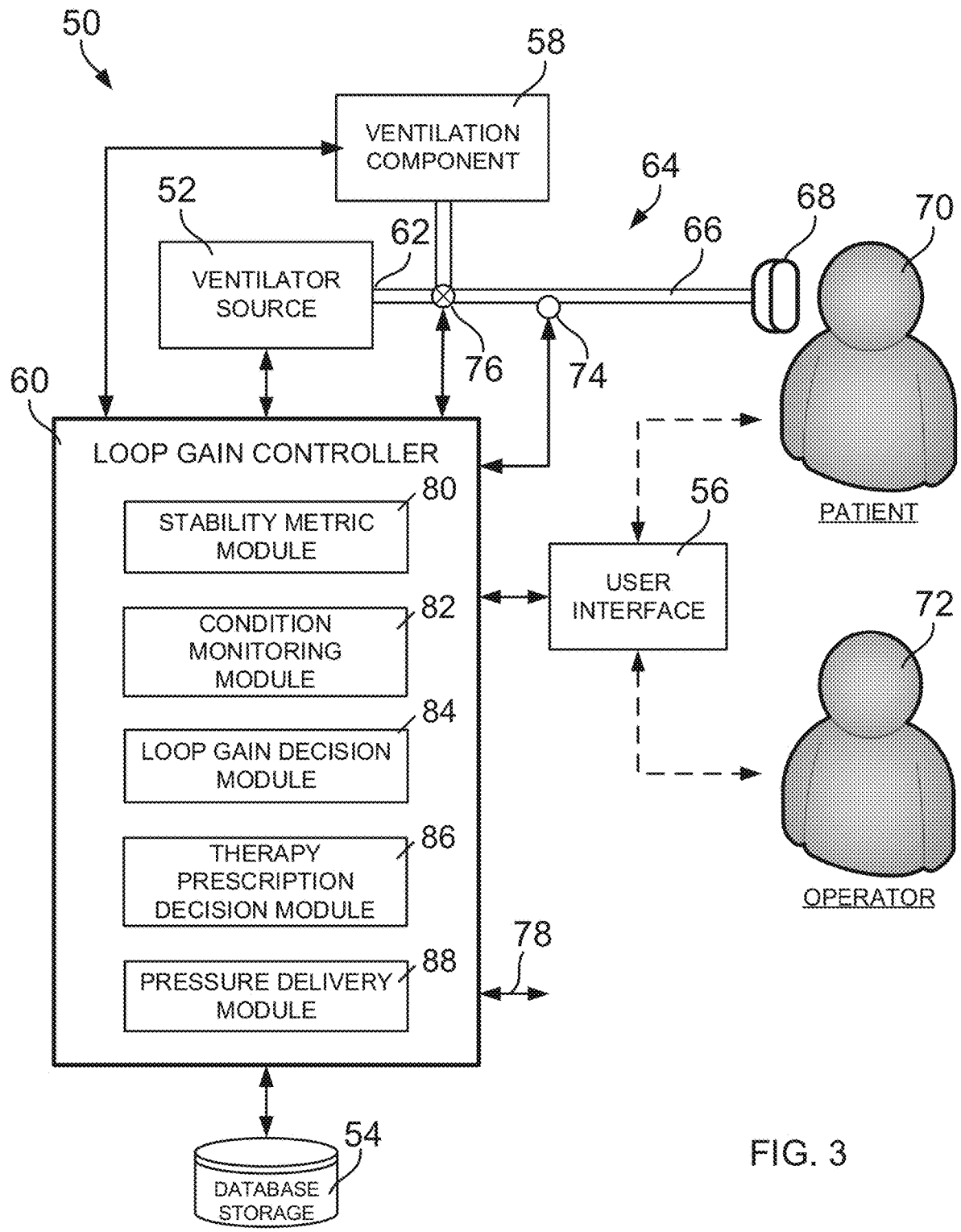
FIG. 3 is a functional block diagram of the system for positive airway pressure therapy utilizing loop gain for ventilation stability according to an embodiment of the present disclosure.

Turning now to FIG. 3, there is shown a functional block diagram of the system 50 for positive airway pressure therapy utilizing loop gain for ventilation stability according to an embodiment of the present disclosure. Positive airway pressure therapy system 50 includes a ventilator source 52, a database 54, a user interface 56, an optional ventilation component 58, and a controller 60 operatively coupled with ventilator source 52, database 54, user interface 56, and optional ventilation component 58. The ventilator source or gas flow generator 52 comprises any suitable ventilator or gas flow generator having an output port 62 configured to output a ventilation gas. The output port 62 is configured to be coupled via a first plurality of ventilation components in a ventilation circuit 64 between the ventilator source 52 and a patient 70.

In other words, the system 50 for delivering a flow of gas to an airway of a patient respiratory system includes a ventilator source or gas flow generator 52, at least one sensor 74, and a loop gain controller 60. The gas flow generator 52 generates the flow of gas and communicates the flow of gas to a patient circuit 64 for delivering the flow of gas to the airway of the patient respiratory system. The at least one sensor 74 generates output signals related to at least one characteristic associated with the flow of gas. The loop gain controller 60 selectively controls the flow of gas to the airway of the patient respiratory system according to a positive airway pressure (PAP) therapy mode, in response to the generated output signals of the at least one sensor 74. Flow into the airway of the patient respiratory system is positive flow and flow out of the airway of the patient respiratory system is negative flow, from the gas flow generator 52 via a patient or ventilation circuit 64. In addition, the PAP therapy mode of system 50 is configured to treat a respiratory system loop gain deficiency corresponding to a ventilation instability by utilizing loop gain for ventilation stability.

PAP therapy system 50 is adapted for use with the patient or ventilation circuit 64 that can comprise a number of various ventilation circuit components. The various ventilation circuit components include at least one or more of a ventilation hose or conduit 66 and a patient interface 68. The patient interface 68 can comprise any one of a variety of patient interfaces to be attached to a patient 70 while receiving ventilation therapy. The patient interface 68 can are either invasively attached to the patient such as an endotracheal tube or tracheostomy tube or non-invasively connected such as a nasal mask, full face mask or nasal cannula. A caregiver or operator 72 may be present during an initial setup of the ventilator system apparatus 50 and/or to assist if needed during an administration of the ventilation therapy to the patient 70. The ventilation circuit components may also include one or more optional ventilation component 58 (e.g., a humidifier, heater, nebulizer, etc.), one or more sensors 74 (e.g., temperature sensor, flow sensor, etc.), and one or more valves 76. In one embodiment, the ventilation hose 66 includes a hose cuff (not shown) at an end thereof that is configured to be coupled to an output port 62 of the ventilator source 52.

With reference still to FIG. 3, the database or storage 54 comprises electronic storage media that electronically stores information. The electronic storage media of database storage 54 can include one or both of system storage that is provided integrally (i.e., substantially non-removable) with system 50 and/or removable storage that is removably connectable to system 50 via, for example, a port (e.g., a USB port, a FireWire port, etc.) or a drive (e.g., a disk drive, etc.). Database or storage 54 may include one or more of optically readable storage media (e.g., optical disks, etc.), magnetically readable storage media (e.g., magnetic tape, magnetic hard drive, floppy drive, etc.), electrical charge-based storage media (e.g., EPROM, EEPROM, RAM, etc.), solid-state storage media (e.g., flash drive, etc.), and/or other electronically readable storage media. Database or storage 54 may store software algorithms, information determined by controller 60, information received via user interface 56, and/or other information that enables system 50 to function properly. Database or storage 54 may be a separate component within system 50, or database storage 54 may be provided integrally with one or more other components of system 50 (e.g., controller 60). Furthermore, database or storage 54 may ideally be contained and maintained (i.e., updated) on a network server, shared computer, be internet based or contained within a third party data center and system 50 may access this data through a telecommunications protocol (e.g., via a wired or wireless communications connection with the third party data center).

User interface 56 is configured to provide an interface between system 50 and a user (e.g., an operator 72, patient or subject 70, a caregiver, a therapy decision-maker, etc.) through which the user can provide information to and receive information from system 50. The user interface 56 enables one or more of data, results, and/or instructions and any other communicable items, collectively referred to as "information," to be communicated between the user and system 50. An example of information that may be conveyed to patient 70 or user 72 is a report detailing trends in the patient's respiratory breathing patterns such as respiratory rate, tidal volume and applied pressures throughout a period during which the patient is receiving (respiratory) therapy. Another example of information that may be conveyed by the patient 70 and/or user 72 is an alarm or unsafe condition detected by system 50. Examples of interface devices suitable for inclusion in user interface 56 include a keypad, buttons, switches, a keyboard, knobs, levers, a display screen, a touch screen, speakers, a microphone, an indicator light, an audible alarm, and a printer. Information may be provided to patient 70 by user interface 56 in the form of auditory signals, visual signals, tactile signals, and/or other sensory signals. In one embodiment, the user interface 56 may be integrated with a removable storage interface provided by database or storage 54. In such an example, information is loaded into system 50 from removable storage (e.g., a smart card, a flash drive, a removable disk, etc.) that enables the user to customize the implementation of system 50. Other techniques for communicating information with system 50 are contemplated as user interface 56.

As noted herein above, controller 60 is operatively coupled with ventilator source or gas flow generator 52, database 54, user interface 56, and optional ventilation component 58. Controller 60 comprises one or more modules that include at least a stability metric module 80, a condition monitoring module 82, a loop gain decision module 84, a therapy prescription decision module 86, and a pressure delivery module 88, as will be discussed further herein. In addition, controller 60 can be configured for a wired or wireless communications connection with a remote device or network, for example, as indicated via reference numeral 78.

In one embodiment, controller 60 comprises one or more of a microprocessor, microcontroller, field programmable gate array (FPGA), integrated circuit, discrete analog or digital circuit components, hardware, software, firmware, or any combination thereof, for performing various functions as discussed herein, further according to the requirements of a given ventilator system apparatus implementation and/or application. Controller 60 can further comprise one or more of the various modules as discussed herein. Additional details regarding the controller 60 will be provided herein below with reference to the Figures. In addition, the modules 80-88 can comprise one or more of an integrated circuit, discrete analog or digital circuit components, hardware, software, firmware, or any combination thereof, for performing various functions as discussed herein, further according to the requirements of a given ventilator system apparatus implementation and/or application. Furthermore, one or more of the modules 80-88 can further comprise various combinations of one or more of the various modules. In addition, it is understood that the described modules may be computer program modules which are rendered in a non-transitory computer-readable medium.

The stability metric module 80 of controller 60 is configured to determine at least one stability metric. The at least one stability metric comprises one or more of (a) a clinical loop gain, (b) a statistical correlate to the clinical loon gain in (a) and (c) a composite metric. The clinical loop gain is defined by:

$$\text{loop gain} = G \cdot \frac{PACO_2 - PICO_2}{\text{lung volume}} \cdot T,$$

where G describes a dynamic responsiveness of a patient ventilation system controller, $PACO_2$-$PICO_2$ is the alveolar-inspired $PCO_2$ gradient for gas exchange, lung volume represents a volume of gas in lungs of the patient available to buffer changes in alveolar $CO_2$, T is a complex timing factor that is determined largely by circulatory delay and partly by a time constant for gas exchange in the lungs. In addition, the statistical correlate to the clinical loop gain in (a) is generated based on breath features, as will be discussed below. Furthermore, the composite metric is generated based on breath features. The breath features for use in generating the statistical correlate or the composite metric of the at least one stability metric, determined via the stability metric module and/or the condition monitoring module, comprise one or more of: i) rate of change of minute ventilation, ii) ventilation overshoot detection, iii) ventilation undershoot detection, iv) period, phase and amplitude of periodic breathing, v) a model dealing with $CO_2$ consumption, vi) a model dealing with sleep stage and/or arousal of central nervous system, vii) simple windowed average minute ventilation, and viii) any combination of the above.

The condition monitoring module 82 of controller 60 is configured to monitor ventilation characteristics of the flow of gas in the patient respiratory system and to provide an output indicative of the monitored ventilation characteristics. The monitored ventilation characteristics at least correspond to an occurrence of sleep disorder breathing (SDB) events in the patient respiratory system.

The loop gain decision module 84 of controller 60 is configured to determine a future ventilation characteristic target and plant gain target based on the determined at least one stability metric and the output from the condition monitoring module. In one embodiment, the future ventilation characteristic and plant gain targets, determined via the loop gain decision module 84, comprise magnitude and/or phase information of the flow of gas in the airway of the patient respiratory system. The future ventilation characteristic and plant gain targets also provide loop gain control, in response to delivery of the therapy command pressure or delivery characteristic, via the pressure delivery module 88. In addition, based on the magnitude and/or phase information, via opposing flow based gain, the future ventilation characteristic and plant gain targets modify, via increasing or decreasing, the loop gain for ventilation stability in the patient respiratory system.

The therapy prescription decision module 86 of controller 60 is configured to determine a therapy command pressure or delivery characteristic based on the determined future ventilation characteristic and plant gain targets, wherein the therapy command pressure or delivery characteristic include a single command pressure or delivery characteristic or a combination of more than one command pressure or delivery characteristic.

The pressure delivery module 88 of controller 60 is configured to control the ventilation source or gas flow generator 52 to deliver the flow of gas to the airway of the patient respiratory system at the determined therapy command pressure or delivery characteristic for a future breath. In other words, pressure delivery module 88 is configured to control an operation of the ventilator source 52 with operating parameters determined as a function of at least an output of the therapy prescription decision module 86. In addition, the outputs of the various modules can be advantageously used to estimate ventilation circuit compliance and thus facilitate circuit compensation accuracy. The improved accuracy of circuit compliance leads to improved estimation of patient parameters, such as flow, tidal volume, and respiratory parameters such as work of breathing (WOB), muscle pressure (Pmus), pressure time product (PTP), intrinsic positive end-expiratory pressure (PEEPi). These parameters are often used to assess patient condition or are employed as an input to a closed loop ventilator control. Each component can have a cataloged compliance or the compliance can be estimated by the volume (i.e., space) of gas inside a given component according to the compressibility of gas and an estimate of the size of the component. Circuit compliance is used to correct distal measurements to their respective proximal values referenced to the patient. Distal measurements are more accurate when they are corrected for losses due to the circuit, including compliance losses. In connection with circuit compliance, the phrase "circuit compensation" as generally used herein refers to the use of circuit compliance for corrective measures. In other words, the ventilator source 52 is configured to output ventilation gas with one or more ventilation properties in response to one or more operating parameters provided via the pressure delivery module 88, thus providing improved patient parameter monitoring and feedback in an improved closed loop ventilator control.

In one embodiment, the future ventilation characteristic and plant gain targets, determined via the loop gain decision module 84, render modifications to plant gain of one or more plant components of the patient respiratory system. In particular, the future ventilation characteristic and plant gain targets render modifications to plant gain via a change in one or more pressure delivery characteristic. The one or more pressure delivery characteristic can include one or more of (i) a baseline pressure, (ii) an inspiratory pressure, and (iii) an expiratory pressure.

In another embodiment, the loop gain decision module 84 further comprises a flow based gain scheduler. The flow based gain scheduler is configured to (i) schedule a flow based gain that is proportional to a magnitude and/or rate of change of a waxing and waning pattern of patient breathing effort. The flow based gain scheduler is further configured to (ii) make additions to or reductions from the patient breathing effort, thus acting in opposition of unstable waxing and waning muscle efforts in the patient respiratory system. In other words, the flow based gain scheduler is configured to (i) schedule a flow based gain that is proportional to a magnitude and/or rate of change of a signal, obtained via the condition monitoring module, that is representative of a sleep disordered breathing pattern, and (ii) make additions to or reductions from the flow of gas, via the pressure delivery module, thereby acting in opposition to unstable breathing efforts in the patient respiratory system. In addition, the therapy prescription decision module 86 is further configured to determine the therapy command pressure or delivery characteristic based upon at least a loop gain input from the flow based gain scheduler. The therapy command pressure or delivery characteristic, when delivered, is configured to generate a flow based gain that provides pressure therapy in such a manner to provide baseline pressure sufficient to overcome obstructive SDB events, or in other words, regulate plant gain and flow based gain configured to normalize loop gain.

In a further embodiment, the future ventilation characteristic target, determined via the loop gain decision module 84 comprises a flow based pressure augmentation that is calculated continuously throughout a breath. The calculated flow based pressure augmentation is a product of (i) an instantaneous patient airway gas flow rate and (ii) a flow based gain factor. In addition, a sign of the instantaneous patient airway gas flow rate is positive during inspiration and negative during expiration. Furthermore, for a positive value of the determined flow based gain factor, the loop gain controller 60 drives ventilation, via the pressure delivery module 88 and the gas flow generator 52, to increase ventilation in the patient respiratory system. For a negative value of the determined flow based gain factor, the loop gain controller 60 restricts ventilation, via the pressure delivery module 88 and the gas flow generator 52, to decrease ventilation in the patient respiratory system.

According to another embodiment, the loop gain decision module 84 is further configured to determine the flow based gain factor, wherein determining the flow based gain factor includes adjusting the flow based gain factor. The determined or adjusted flow based gain factor is based on monitored conditions of the patient respiratory system in a current phase of instability of a patient breath cycle in response to the generated output signals of the at least one sensor 74. In addition, the loop gain decision module 84 adjusts the flow based gain factor for a given disease state and the adjustment occurs only while conditions of the respective disease state are occurring in the patient respiratory system. In another embodiment, the condition monitoring module 82 is further configured to collect and monitor output signals of the at least one sensor 74 which correspond to inputs for respiratory system loop gain determination in a positive airway pressure (PAP) therapy.

Figure 4:
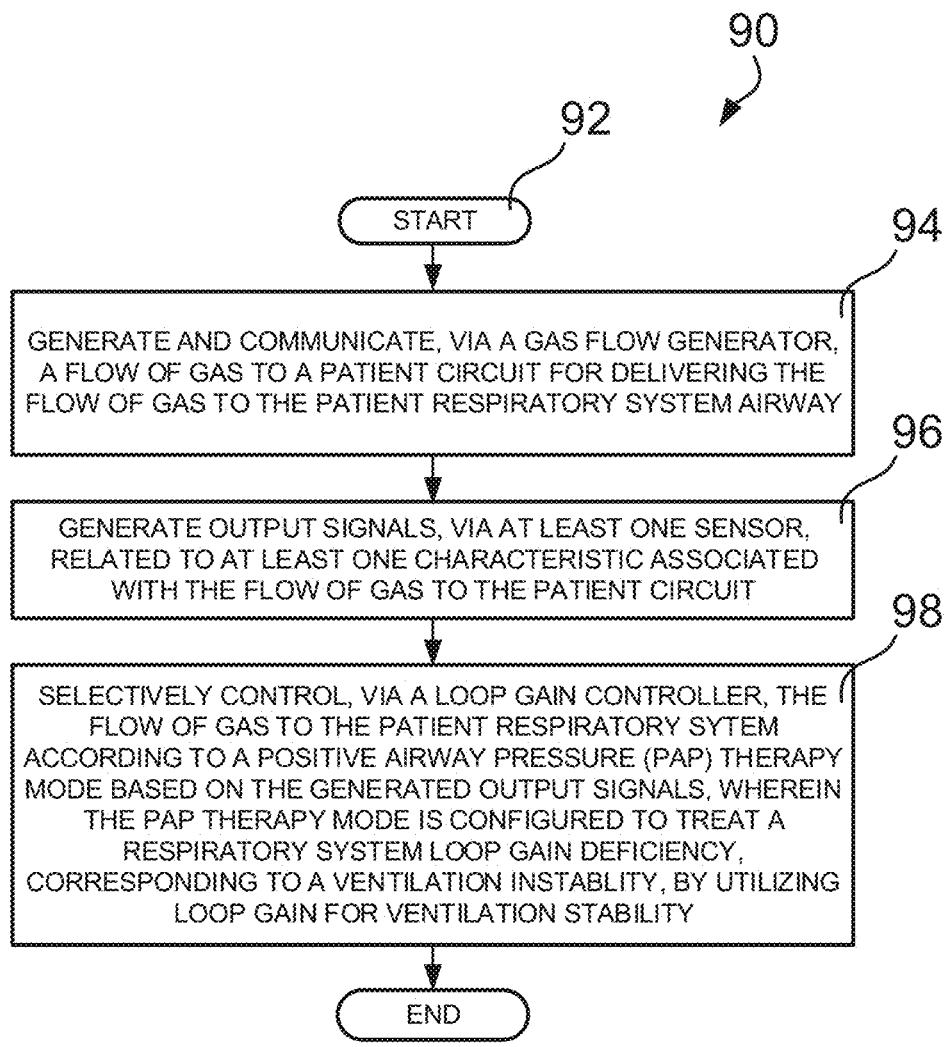
FIG. 4 is a flow diagram view of a method for positive airway pressure therapy utilizing loop gain for ventilation stability according to an embodiment of the present disclosure.

Referring now to FIG. 4, a flow diagram view is shown of a method 90 for positive airway pressure therapy utilizing loop gain for ventilation stability according to an embodiment of the present disclosure. The method 90 for delivering a flow of gas to an airway of a patient respiratory system comprises: generating the flow of gas (at Step 94), generating output signals (at Step 96), and selectively controlling, via a loop gain controller 60 (FIG. 3), the flow of gas to the airway of the patient respiratory system (at Step 98). Generating and communicating the flow of gas to a patient circuit (at Step 94) is accomplished via a gas flow generator 54 (FIG. 3), further for delivering the flow of gas to the airway of the patient respiratory system. Generating output signals (at Step 96) related to at least one characteristic associated with the flow of gas is accomplished via at least one sensor 74 (FIG. 3). Selectively controlling the flow of gas to the airway of the patient respiratory system is accomplished via a loop gain controller 60 according to a positive airway pressure (PAP) therapy mode, further in response to the generated output signals via the at least one sensor 74. Flow into the airway of the patient respiratory system is positive flow and flow out of the airway of the patient respiratory system is negative flow, from the gas flow generator 52 via the patient circuit 64. The PAP therapy mode is configured to treat a respiratory system loop gain deficiency corresponding to a ventilation instability by utilizing loop gain for ventilation stability.

Figure 5:
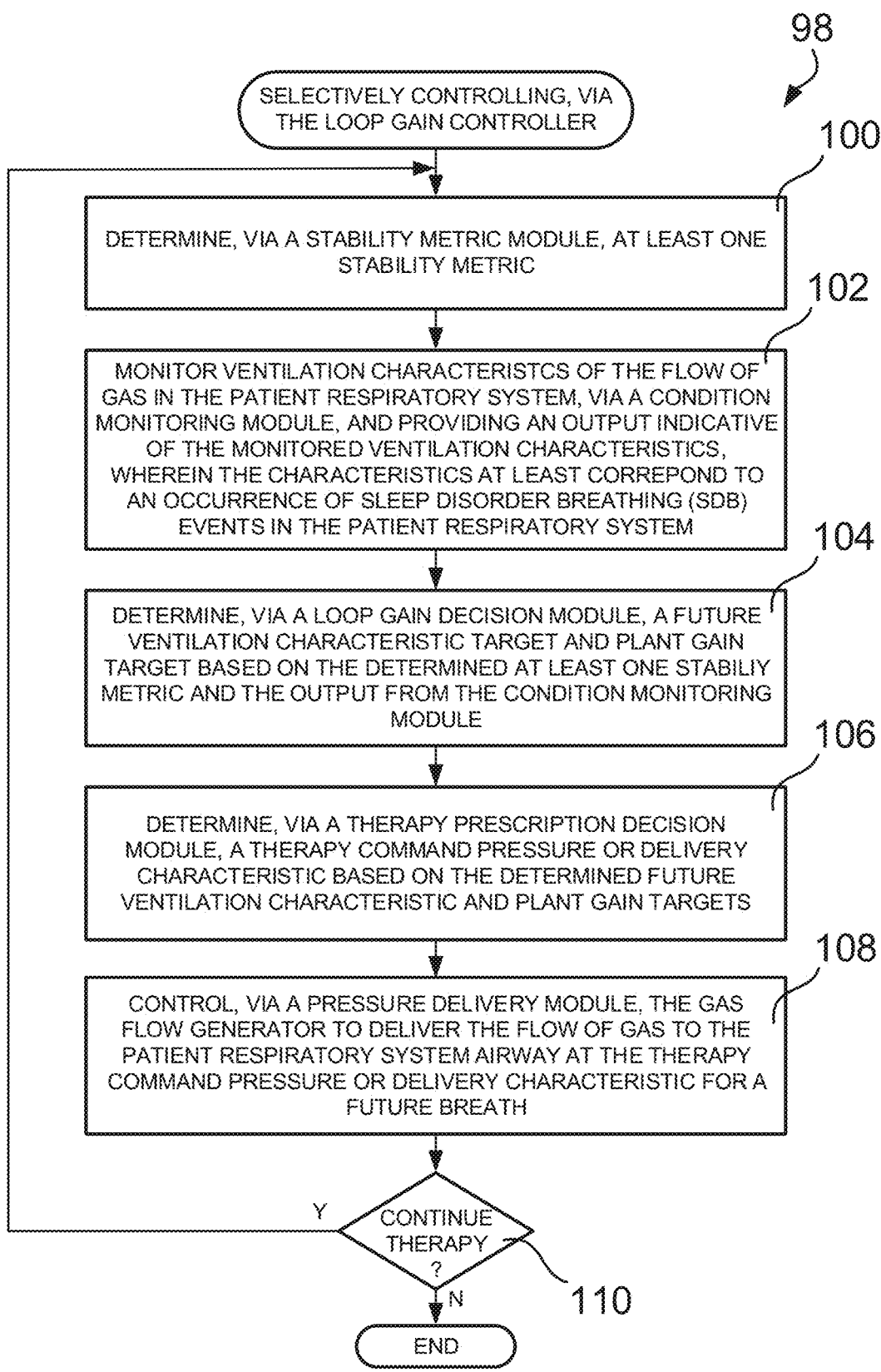
FIG. 5 is a further flow diagram view of a portion of the method for positive airway pressure therapy utilizing loop gain for ventilation stability according to an embodiment of the present disclosure.

With reference now to FIG. 5, there is shown a further flow diagram view of a portion of the method for positive airway pressure therapy, corresponding to Step 98 (FIG. 4) of selectively controlling, via the loop gain controller 60, utilizing loop gain for ventilation stability according to an embodiment of the present disclosure. The method includes wherein selectively controlling, via the loop gain controller 60, (Step 98) comprises: (a) determining, via a stability metric module 80 (FIG. 3), at least one stability metric (Step 100), (b) monitoring, via a condition monitoring module 82, ventilation characteristics of the flow of gas in the patient respiratory system and providing an output indicative of the monitored ventilation characteristics (Step 102), wherein the monitored ventilation characteristics at least correspond to an occurrence of sleep disorder breathing (SDB) events in the patient respiratory system, (c) determining, via a loop gain decision module 84, a future ventilation characteristic target and plant gain target based on the determined at least one stability metric and the output from the condition monitoring module (Step 104), (d) determining, via a therapy prescription decision module 86, a therapy command pressure or delivery characteristic based on the determined future ventilation characteristic and plant gain targets (Step 106), wherein the therapy command pressure or delivery characteristic include as single command pressure or delivery characteristic or a combination of more than one command pressure or delivery characteristic, and (e) controlling, via a pressure delivery module 88, the gas flow generator 52 to deliver the flow of gas to the airway of the patient respiratory system at the therapy command pressure or delivery characteristic for a future breath (Step 108).

Subsequent to delivering the flow of gas in step 108, the loop gain controller queries whether or not to continue therapy (Step 110). In response to continuing therapy, the method returns to step 100, with determining, via the stability metric module 80, at least one stability metric. On the other hand, in response to not continuing therapy, the method ends.

According to yet another embodiment, the method includes wherein the future ventilation characteristic and plant gain targets, determined via the loop gain decision module 84, (i) comprise magnitude and/or phase information of the flow of gas in the airway of the patient respiratory system, (ii) provide loop gain control, in response to delivery of the therapy command pressure or delivery characteristic, via the pressure delivery module 88, and (iii) based on the magnitude and/or phase information, via opposing flow based gain, modify, via increasing or decreasing, the loop gain for ventilation stability in the patient respiratory system. In addition, the future ventilation characteristic and plant gain targets, determined via the loop gain decision module 84, render modifications to plant gain of one or more plant components of the patient respiratory system via a change in one or more pressure delivery characteristic. The one or more pressure delivery characteristic includes one or more of (i) a baseline pressure, (ii) an inspiratory pressure, and (iii) an expiratory pressure.

According to still further embodiment, the method includes wherein selectively controlling, via the loop gain controller 60, further comprises: (c)(i) scheduling, via a flow based gain scheduler of the loop gain decision module, a flow based gain that is proportional to a magnitude and/or rate of change of a waxing and waning pattern of patient breathing effort, and (c)(ii) making additions to or reductions from the patient breathing effort, via the determined future ventilation characteristic target and plant gain target, thus acting in opposition of unstable waxing and waning muscle efforts in the patient respiratory system. In a further embodiment, the method includes wherein selectively controlling, via the loop gain controller 60, further comprises: (d)(i) determining, via the therapy prescription decision module 86, the therapy command pressure or delivery characteristic based upon at least a loop gain input from the flow based gain scheduler, wherein the therapy command pressure or delivery characteristic, when delivered, is configured to generate a flow based gain that provides pressure therapy in such a manner to provide baseline pressure sufficient to overcome obstructive SDB events, or in other words, regulate plant gain and flow based gain configured to normalize loop gain.

The embodiments of the present disclosure advantageously provide a PAP device with an integrated ventilation stability feature in which the stability is based on loop gain. Various examples of PAP interventions and corresponding mechanisms of reduced ventilatory instability (i.e., loop gain) can be briefly summarized as follows. For the intervention of optimized treatment in heart failure, the corresponding mechanism of reduced ventilatory instability presumably lowers chemosensitivity and reduces circulatory delays. For the intervention of continuous positive airway pressure (CPAP), the corresponding mechanism of reduced ventilatory instability (i) increases lung volume, (ii) provides possible effect on cardiogenic pulmonary oedema and associated effects on chemosensitivity, and (iii) provides possible long-term effects on cardiac function and circulatory delay. For the intervention of supplemental oxygen, the corresponding mechanism of reduced ventilatory instability lowers carotid-body chemosensitivity. For the intervention of ventilatory stimulants (e.g., acetazolamide and supplemental carbon dioxide), the corresponding mechanism of reduced ventilatory instability comprises acetazolamide lowering alveolar $PCO_2$ and supplemental $CO_2$ raising inspired $PCO_2$, with both reducing the alveolar inspired $PCO_2$ gradient. For the intervention of body position (e.g., lateral or upright, versus supine), the corresponding mechanism of reduced ventilatory instability increases lung volume. Additional interventions and corresponding mechanisms of reduced ventilatory instability are possible.

Although a few exemplary embodiments have been described in detail above, those skilled in the art will readily appreciate that many modifications are possible in the exemplary embodiments without materially departing from the novel teachings and advantages of the embodiments of the present disclosure. Accordingly, all such modifications are intended to be included within the scope of the embodiments of the present disclosure as defined in the following claims. In the claims, means-plus-function clauses are intended to cover the structures described herein as performing the recited function and not only structural equivalents, but also equivalent structures.

In addition, any reference signs placed in parentheses in one or more claims shall not be construed as limiting the claims. The word "comprising" and "comprises," and the like, does not exclude the presence of elements or steps other than those listed in any claim or the specification as a whole. The singular reference of an element does not exclude the plural references of such elements and vice-versa. One or more of the embodiments may be implemented by means of hardware comprising several distinct elements, and/or by means of a suitably programmed computer. In a device claim enumerating several means, several of these means may be embodied by one and the same item of hardware. The mere fact that certain measures are recited in mutually different dependent claims does not indicate that a combination of these measures cannot be used to an advantage.

The invention claimed is:

1. A system for delivering a flow of gas to an airway of a patient respiratory system, the system comprising:
   a gas flow generator configured to generate the flow of gas, wherein the gas flow generator is further configured to communicate the flow of gas to a patient circuit;
   at least one sensor configured to generate output signals related to at least one characteristic associated with the flow of gas; and
   a loop gain controller configured to selectively control the flow of gas from the gas flow generator via the patient circuit, according to a positive airway pressure (PAP) therapy mode which targets loop gain deficiency, in response to the generated output signals, wherein the loop gain controller comprises:
   (a) a stability metric module configured to determine at least one ventilation stability metric, descriptive of ventilation stability, which correlates to a loop gain,
   (b) a condition monitoring module configured to monitor ventilation characteristics of the flow of gas and to provide an output indicative of the monitored ventilation characteristics, wherein the monitored ventilation characteristics at least correspond to an occurrence of sleep disorder breathing (SDB) events,
   (c) a loop gain decision module configured to determine a future ventilation characteristic target and plant gain target based on the determined at least one ventilation stability metric and the output from the condition monitoring module, wherein the future ventilation characteristic target and plant gain target are specific to managing ventilation stability via treating a corresponding loop gain deficiency,
   (d) a therapy prescription decision module configured to determine a therapy command pressure or delivery characteristic based on the determined future ventilation characteristic and plant gain targets, and
   (e) a pressure delivery module configured to control the gas flow generator to deliver the flow of gas at the determined therapy command pressure or delivery characteristic for a future breath to overcome the loop gain deficiency and provide ventilation stability,
   wherein the future ventilation characteristic target, determined via the loop gain decision module comprises a flow based pressure augmentation that is calculated continuously throughout a breath, and wherein the calculated flow based pressure augmentation is a product of (i) an instantaneous patient airway gas flow rate and (ii) a flow based gain factor, wherein the loop gain decision module is further configured to determine the flow based gain factor, and wherein the loop gain decision module adjusts the flow based gain factor for a given disease state and the adjustment occurs only while conditions, determined via the condition monitoring module, of the respective disease state are occurring.

2. The system according to claim 1, wherein the at least one stability metric comprises one or more of:
   (a) a clinical loop gain as defined by:

$$\text{loop gain} = G \cdot \frac{PACO_2 - PICO_2}{\text{lung volume}} \cdot T,$$

where G describes a dynamic responsiveness of a respiratory system controller, $PACO_2$-$PICO_2$ is the alveolar-inspired $PCO_2$ gradient for gas exchange, lung volume represents a volume of gas in lungs of the patient available to buffer changes in alveolar $CO_2$, T is a complex timing factor that is determined largely by circulatory delay and partly by a time constant for gas exchange in the lungs;
   (b) a statistical correlate to the clinical loop gain in (a), wherein the statistical correlate is generated based on breath features; and
   (c) a composite metric, wherein the composite metric corresponds with a model representing loop gain, wherein the model is constructed via artificial intelligence, machine learning, or a combination thereof, based on breath features.

3. The system according to claim 2, wherein the breath features for use in generating the statistical correlate or the composite metric of the at least one ventilation stability metric, determined via the stability metric module, comprise one or more of:
   i) rate of change of minute ventilation,
   ii) ventilation overshoot detection,
   iii) ventilation undershoot detection,
   iv) period, phase and amplitude of periodic breathing,
   v) a model dealing with $CO_2$ consumption,
   vi) a model dealing with sleep stage and/or arousal of central nervous system,
   vii) simple windowed average minute ventilation, and
   viii) any combination of the above.

4. The system according to claim 1, wherein the future ventilation characteristic and plant gain targets, determined via the loop gain decision module, (i) comprise magnitude and/or phase information of the flow of gas, (ii) provide loop gain control, in response to delivery of the therapy command pressure or delivery characteristic, via the pressure delivery module, and (iii) based on the magnitude and/or phase information, via opposing flow based gain, modify, via increasing or decreasing, the loop gain for ventilation stability.

5. The system according to claim 1, wherein the future ventilation characteristic and plant gain targets, determined via the loop gain decision module, render modifications to plant gain of one or more plant components via a change in one or more pressure delivery characteristic.

6. The system according to claim 1, wherein the loop gain decision module further comprises a flow based gain scheduler specific to managing ventilation stability via treating the corresponding loop gain deficiency.

7. The system according to claim 6, wherein the flow based gain scheduler is configured to (i) schedule a flow based gain that is proportional to a magnitude and/or rate of change of a signal, obtained via the condition monitoring module, that is representative of a sleep disordered breathing pattern, and (ii) make additions to or reductions from the flow of gas, via the pressure delivery module, thereby acting in opposition to unstable breathing efforts in the patient respiratory system.

8. The system according to claim 6, wherein the therapy prescription decision module is further configured to determine the therapy command pressure or delivery characteristic based upon at least a loop gain input from the flow based gain scheduler, wherein the therapy command pressure or delivery characteristic, when delivered, is configured to generate a flow based gain that provides pressure therapy in such a manner to provide baseline pressure sufficient to overcome obstructive SDB events, or regulate plant gain and flow based gain configured to normalize loop gain.

9. The system according to claim 1, wherein a sign of the instantaneous patient airway gas flow rate is positive during inspiration and negative during expiration.

10. The system according to claim 1, wherein for a positive value of the flow based gain factor, the loop gain controller drives ventilation, via the pressure delivery module and the gas flow generator, to increase ventilation, and wherein for a negative value of the determined flow based gain factor, the loop gain controller restricts ventilation, via the pressure delivery module and the gas flow generator, to decrease ventilation.

11. The system according to claim 1, wherein determining the flow based gain factor includes adjusting the flow based gain factor, and wherein the determined or adjusted flow based gain factor is based on monitored conditions in a current phase of instability of a breath cycle in response to the generated output signals.

12. The system according to claim 1, wherein the condition monitoring module is further configured to collect and monitor output signals of the at least one sensor which correspond to inputs for respiratory system loop gain determination in the positive airway pressure (PAP) therapy mode.

13. A system for delivering a flow of gas to an airway of a patient respiratory system, the system comprising:
   a gas flow generator configured to generate the flow of gas, wherein the gas flow generator is further configured to communicate the flow of gas to a patient circuit;
   at least one sensor configured to generate output signals related to at least one characteristic associated with the flow of gas; and
   a loop gain controller configured to selectively control the flow of gas from the gas flow generator via the patient circuit, according to a positive airway pressure (PAP) therapy mode which targets loop gain deficiency, in response to the generated output signals, wherein the loop gain controller comprises:
      (a) a stability metric module configured to determine at least one ventilation stability metric, descriptive of ventilation stability, which correlates to a loop gain,
      (b) a condition monitoring module configured to monitor ventilation characteristics of the flow of gas and to provide an output indicative of the monitored ventilation characteristics, wherein the monitored ventilation characteristics at least correspond to an occurrence of sleep disorder breathing (SDB) events,
      (c) a loop gain decision module configured to determine a future ventilation characteristic target and plant gain target based on the determined at least one ventilation stability metric and the output from the condition monitoring module, wherein the future ventilation characteristic target and plant gain target are specific to managing ventilation stability via treating a corresponding loop gain deficiency,
      (d) a therapy prescription decision module configured to determine a therapy command pressure or delivery characteristic based on the determined future ventilation characteristic and plant gain targets, and
      (e) a pressure delivery module configured to control the gas flow generator to deliver the flow of gas at the determined therapy command pressure or delivery characteristic for a future breath to overcome the loop gain deficiency and provide ventilation stability,
wherein the future ventilation characteristic target, determined via the loop gain decision module comprises a flow based pressure augmentation that is calculated continuously throughout a breath, and wherein the calculated flow based pressure augmentation is a product of (i) an instantaneous patient airway gas flow rate and (ii) a flow based gain factor, wherein the loop gain decision module adjusts the flow based gain factor for a given disease state and the adjustment occurs only while conditions, determined via the condition monitoring module, of the respective disease state are occurring.

14. A method for delivering a flow of gas to an airway of a patient respiratory system, the method comprising:
   generating the flow of gas, via a gas flow generator and communicating, via the gas flow generator, the flow of gas to a patient circuit;
   generating output signals, via at least one sensor, related to at least one characteristic associated with the flow of gas; and
   selectively controlling, via a loop gain controller, the flow of gas from the gas flow generator via the patient circuit, according to a positive airway pressure (PAP) therapy mode which targets loop gain deficiency, in response to the generated output signals, wherein selectively controlling, via the loop gain controller, comprises:
      (a) determining, via a stability metric module, at least one ventilation stability metric, descriptive of ventilation stability, which correlates to a loop gain,
      (b) monitoring, via a condition monitoring module, ventilation characteristics of the flow of gas and providing an output indicative of the monitored ventilation characteristics, wherein the monitored ventilation characteristics at least correspond to an occurrence of sleep disorder breathing (SDB) events,
      (c) determining, via a loop gain decision module, a future ventilation characteristic target and plant gain target based on the determined at least one ventilation stability metric and the output from the condition monitoring module, wherein the future ventilation characteristic target and plant gain target are specific to managing ventilation stability via treating a corresponding loop gain deficiency,
      (d) determining, via a therapy prescription decision module, a therapy command pressure or delivery characteristic based on the determined future ventilation characteristic and plant gain targets, and
      (e) controlling, via a pressure delivery module, the gas flow generator to deliver the flow of gas at the therapy command pressure or delivery characteristic for a future breath to overcome the loop gain deficiency and provide ventilation stability,
wherein the future ventilation characteristic target, determined via the loop gain decision module comprises a flow based pressure augmentation that is calculated continuously throughout a breath, and wherein the calculated flow based pressure augmentation is a product of (i) an instantaneous patient airway gas flow rate and (ii) a flow based gain factor, and adjusting, via the loop gain decision module, the flow based gain factor for a given disease state, wherein the adjustment occurs only while conditions, determined via the condition monitoring module, of the respective disease state are occurring.

15. The method according to claim 14, wherein the at least one stability metric comprises one or more of:
   (a) a clinical loop gain as defined by:

$$\text{loop gain} = G \cdot \frac{PACO_2 - PICO_2}{\text{lung volume}} \cdot T$$

where G describes a dynamic responsiveness of a respiratory system controller, $PACO_2$-$PICO_2$ is the alveolar-inspired $PCO_2$ gradient for gas exchange, lung volume represents a volume of gas in lungs of the patient available to buffer changes in alveolar $CO_2$, T is a complex timing factor that is determined largely by circulatory delay and partly by a time constant for gas exchange in the lungs;

(b) a statistical correlate to the clinical loop gain in (a), wherein the statistical correlate is generated based on breath features; and (c) a composite metric, wherein the composite metric corresponds with a model representing loop gain, wherein the model is constructed via artificial intelligence, machine learning, or a combination thereof, based on breath features.

16. The method according to claim 15, wherein the breath features for use in generating the statistical correlate or the composite metric of the at least one ventilation stability metric, determined via the stability metric module, comprise one or more of:

i) rate of change of minute ventilation,
    ii) ventilation overshoot detection,
    iii) ventilation undershoot detection,
    iv) period, phase and amplitude of periodic breathing,
    v) a model dealing with $CO_2$ consumption,
    vi) a model dealing with sleep stage and/or arousal of central nervous system,
    vii) simple windowed average minute ventilation, and
    viii) any combination of the above.

17. The method according to claim 14, wherein the future ventilation characteristic and plant gain targets, determined via the loop gain decision module, (i) comprise magnitude and/or phase information of the flow of gas, (ii) provide loop gain control, in response to delivery of the therapy command pressure or delivery characteristic, via the pressure delivery module, and (iii) based on the magnitude and/or phase information, via opposing flow based gain, modify, via increasing or decreasing, the loop gain for ventilation stability.

18. The method according to claim 14, wherein the future ventilation characteristic and plant gain targets, determined via the loop gain decision module, render modifications to plant gain of one or more plant components via a change in one or more pressure delivery characteristic.

19. The method according to claim 14, wherein selectively controlling, via the loop gain controller, further comprises:

(c)(i) scheduling, via a flow based gain scheduler of the loop gain decision module specific to managing ventilation stability via treating the corresponding loop gain deficiency, a flow based gain that is proportional to a magnitude and/or rate of change of a signal, obtained via the condition monitoring module, that is representative of a sleep disordered breathing pattern, and (c)(ii) making additions to or reductions from the flow of gas, via the determined future ventilation characteristic target and plant gain target, thereby acting in opposition to unstable breathing efforts in the patient respiratory system; or (d)(i) determining, via the therapy prescription decision module (86), the therapy command pressure or delivery characteristic based upon at least a loop gain input from the flow based gain scheduler, wherein the therapy command pressure or delivery characteristic, when delivered, is configured to generate a flow based gain that provides pressure therapy in such a manner to provide baseline pressure sufficient to overcome obstructive SDB events, or regulate plant gain and flow based gain configured to normalize loop gain.

\* \* \* \* \*